United States Patent [19]

Kapitanov et al.

[11] 4,122,989

[45] Oct. 31, 1978

[54] INSTRUMENT FOR SUTURING WITH METAL STAPLES

[76] Inventors: Nikolai N. Kapitanov, ulitsa Iriny Levchenko, 3, kv. 9; Svetlana V. Kolosova, Zarevy proezd, 15, kv. 28; Vyacheslav D. Kolesnikov, Grokholsky pereulok, 30, korpus 2, kv. 65, all of Moscow; Vladimir P. Kharchenko, Krasnogorsky raion, p/o Stepanovskoe, 18, kv. 28, Moskovskaya oblast, all of U.S.S.R.

[21] Appl. No.: 743,000

[22] Filed: Nov. 18, 1976

[30] Foreign Application Priority Data

Dec. 19, 1975 [SU] U.S.S.R. .............................. 2301823

[51] Int. Cl.² .............................................. B25C 5/02
[52] U.S. Cl. ...................................... 227/108; 227/19
[58] Field of Search ........................... 227/19, 83, 108

[56] References Cited

U.S. PATENT DOCUMENTS

| | | | |
|---|---|---|---|
| 2,427,028 | 9/1947 | Spencer | 227/108 |
| 2,770,804 | 11/1956 | Schafroth | 227/108 |
| 2,874,384 | 2/1959 | Krone | 227/19 |
| 3,269,631 | 8/1966 | Takaro | 227/19 |
| 3,482,428 | 12/1969 | Kapitanov et al. | 227/19 |

Primary Examiner—Granville Y. Custer, Jr.
Attorney, Agent, or Firm—Steinberg & Blake

[57] ABSTRACT

A surgical instrument for suturing tissue with metal staples includes an anvil unit which has two elongated jaws aligned with each other and having inner surfaces facing each other and formed with longitudinal guiding grooves for a staple. The front ends of the jaws carry anvils for bending the tips of the staples, said anvils being shaped as curved needles, having tips facing each other and formed with longitudinal grooves which are extensions of said guiding grooves of the jaws. The jaws can be releasably connected to each other in a position in which the longitudinal grooves of the jaws are approximately parallel to each other. A detachable staple-driving unit has a frame mounted on the jaws, provided with grooves for a staple and a staple driving member with a lever for operating the same.

The instrument, in accordance with the invention, ensures suturing of bone tissues when the access to the surgical field of operation is difficult, and can be predominantly used in operations on the sternum and ribs for connecting sternal fragments of both equal and varying thickness and for connecting ribs without incising the pleural cavity.

7 Claims, 12 Drawing Figures

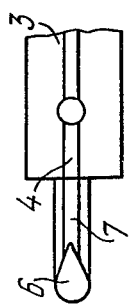
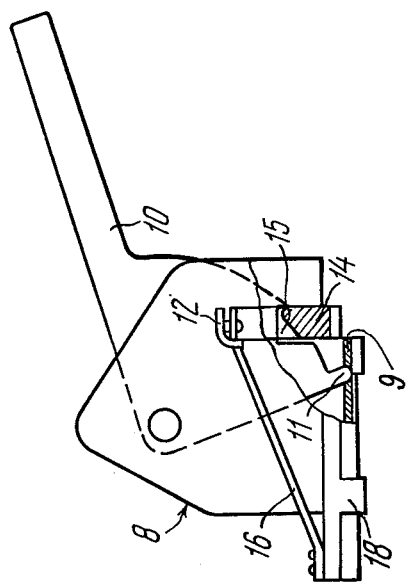
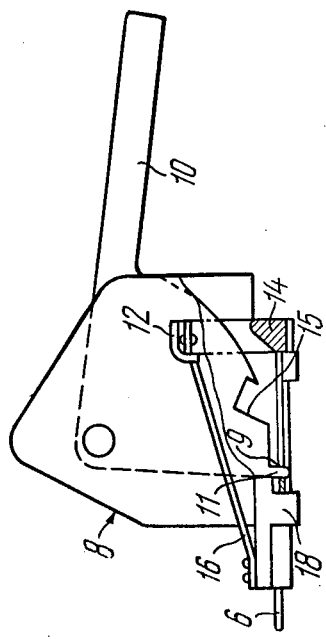
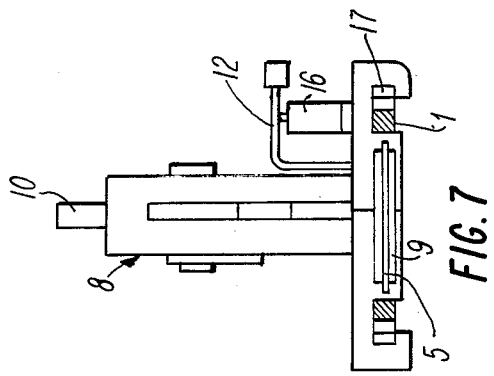
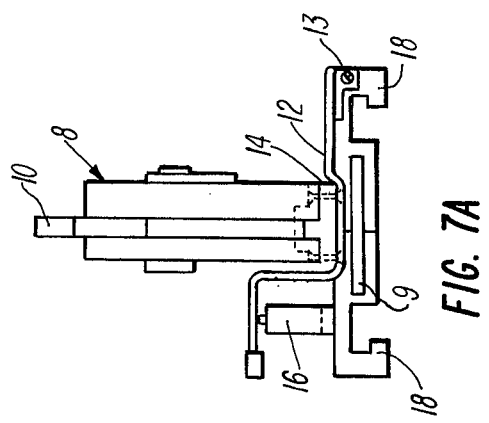

INSTRUMENT FOR SUTURING WITH METAL STAPLES

The present invention relates to medical equipment, and, more specifically, to surgical instruments for suturing tissues with metal staples, that can be used for connecting osseous biological tissues, such as ribs and the sternum. Said instrument can be used for osteosynthesis operations, like suturing ribs without incising the pleural cavity, fixing severed ribs to the sternum, connecting the sternum following a longitudinal or transverse division thereof, suturing osseous fragments of equal and varying thickness.

There is known an instrument for suturing tissues with metal staples. This instrument features two elongated jaws extending along each other. The inner surfaces of said jaws have guiding recesses for the staples. The front ends of said jaws bear anvils shaped like needles bent at approximately 90°, the tips thereof facing each other and containing longitudinal recesses on the inner surfaces that serve as an extension of said guiding recesses of said jaws and are intended for bending the tips of the staples. A means is affixed to the jaws, featuring a magazine with recesses for staples, and an actuating member with a lever to propel the staples towards said anvil is likewise affixed to said jaws.

The rear ends of the jaws are articulated on a pin so that the jaws form forceps.

Said jaws can be both separable and non-separable.

A spring spreading the jaws is affixed to one of said jaws.

Each jaw has a transverse groove for the advancement of said magazine, and a device for fixing said magazine.

The needle-shaped anvils are rigidly connected with the jaws, but may be replaceable as well.

The magazine has a longitudinal recess for the passage of said actuating member intended for propelling the staples.

The actuating member serves likewise for locking the jaws prior to the suturing procedure, for which purpose recesses entering the lugs on the jaws are provided thereon, this structure serving also for starting the mechanism for automated magazine advancement. A staple is inserted into each recess of said magazine so as to face, with the tips of said staple, the needle-shaped anvils when placed on the jaw. Prior to placing the magazine into the transverse groove of the jaw, the actuating member is placed into the jaw spreading position, i.e. a position wherein the actuating member recesses are displaced from the longitudinal lugs of said jaws. The spring spreads the jaws. The magazine is inserted into the transverse grooves of the jaws. The surgeon pierces the edges of the tissues to be connected with the needle-shaped anvils and brings the jaws close to each other, thereby connecting the edges of the tissue in question. Thereafter the actuating member is advanced towards the needle-shaped anvils, and the staples are ejected. The tips of the staples reaching the curve of the needle-shaped anvils bend in the curved parts thereof. The tissue is thus connected with sutures. The instrument is removed from the connected tissues in the following way. The actuating member is returned to the initial position, i.e. a position wherein the recesses thereof are displaced from the lugs of the jaws. The jaws tend to spread under the effect of the spring. Keeping the edges of the tissue in place the needle-shaped anvils are removed therefrom.

The described surgical instrument provides convenient access to the surgical field of operation. The gear of the actuating member, however, is manually operated, the piercing effort being directly transmitted from the surgeon's hand to the actuating member and the staple, which does not permit developing a sufficient force to insert the needle-shaped anvils into bone tissues, and hence, permits suturing soft tissues only.

Besides, since the body of the instrument is shaped as a forceps, the mobilization of bone tissues is inconvenient since the needles slip on the bone tissue.

It is an object of the invention to provide a surgical instrument for suturing tissues with metal staples that provides convenient access to the surgical field of operation, and, simultaneously, provides a greater force for said suturing, so as to render the instrument useful for suturing poorly accessible bone tissues, for example, ribs, without incising the pleural cavity, for fixing severed ribs to the sternum, for suturing the sternum following a longitudinal or transverse division thereof, as well as for suturing bone fragments of equal or varying thickness.

This above object is attained is that in a surgical instrument for suturing tissues with metal staples, there is an anvil unit including two elongated jaws extending essentially along each other, the inner surfaces thereof being provided with longitudinal guiding grooves for a staple, and the front end thereof having affixed thereto anvils shaped like needles curved at approximately 90°, the tips thereof facing each other, with the anvils having longitudinal grooves on the inner surfaces, that serve as extensions of said guiding grooves of said jaws and are intended for bending the tips of the staples. A staple-driving unit is provided with means for locating a staple to be guided by said jaws and includes a staple-driving member with a lever for propelling said staple towards said anvil. In accordance with the invention, said jaws are provided with a means for releasably holding them in a position wherein the longitudinal grooves on the inner surfaces of the jaws are approximately parallel to each other. The means for locating the staple and the staple-driving member with the lever are assembled in a common detachable frame.

Embodying said instrument with two separable jaws ensures convenient access to the tissues to be sutured. The instrument permits suturing bone tissues, e.g. ribs with the sternum, permitting thereby suturing ribs without incising the pleural cavity. Suturing with the aid of the instrument in question is realized without compressing the bone tissues, without detaching the periosteum, which permits minimizing the traumatization of the bone tissues being connected.

It is expedient to make the means for releasably holding the jaws parallel to each other as a separable hinge located approximately in mid-jaw position, and a spreader pivotally mounted on the rear end of one of said jaws and carrying a swingable loop for surrounding the rear end of the other jaw.

Such releasable holding means is simple in design and convenient in handling.

It is desirable to fix the needle-shaped anvils on the jaws in an adjustable manner permitting fixation thereof at varying distances between the curved portions thereof and the front ends of the jaws.

The possibility of varying the distance between the needle-shaped anvils and the front ends of the jaws permits suturing bone fragments of both equal and varying thickness, which increases the potential of the instrument.

The invention will be further understood from the following description of an exemplary embodiment thereof with reference of the accompanying drawings, wherein:

FIG. 4 is an enlarged view of FIG. 3, taken substantially along arrow IV;

FIG. 5 is a partly sectional side elevation view of a detachable staple-driving unit of the instrument, in accordance with the invention, with a staple-driving member in a rear position;

FIG. 6 is a partly sectional side view of the unit of FIG. 5, with the staple-driving member in a forward position;

FIG. 7 is a sectional view taken substnatially along line VII—VII of FIG. 1;

FIG. 7A is an end elevation of the structure shown in FIG. 5 as seen from the right of FIG. 5;

Figure 1:
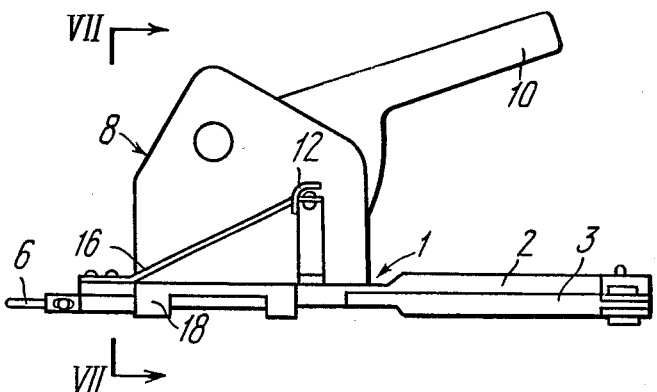
FIG. 1 is a side elevation view of a surgical instrument, in accordance with the invention, intended for suturing tissues with metal staples.
Figure 2:
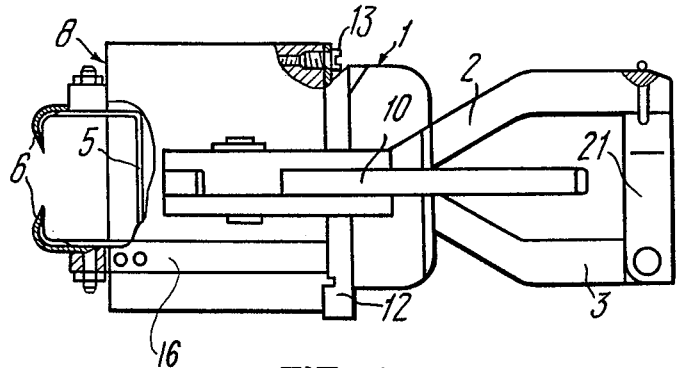
FIG. 2 is a partly sectional plan view of the instrument of FIG. 1.

Referring now to the drawings, the surgical instrument for suturing tissues with metal staples comprises an anvil unit 1 (FIGS. 1, 2 and 3) including two elongated jaws 2 and 3 extending essentially along each other. The inner surfaces of the jaws 2 and 3 contain longitudinal guiding grooves 4 (FIGS. 3 and 4) for a metal staple 5 (FIG. 2). On the front ends of the jaws 2 and 3, anvils 6 are affixed featuring needles curved at approximately 90°, the tips thereof facing each other and serving for bending the tips of the staple 5. The inner surfaces of the needle-shaped anvils 6 are provided with longitudinal grooves 7 (FIGS. 3 and 4) serving as extensions of the guiding grooves 4. A detachable frame 8 of a staple-driving unit (FIGS. 2 and 5) serves for holding the staple 5 (FIG. 2) and is provided with grooves therefor. The detachable frame 8 also includes a staple-driving member 9 (FIGS. 5 and 6) located in grooves in the frame 8 and serving for ejecting the staple 5 (FIG. 7), and a drive for the staple-driving member 9 includes lever 10 having a lug 11 entering into an aperture in said member 9, as depicted in FIGS. 5 and 6.

Said detachable frame 8 also holds a blocking device for the member 9, made as a profiled springy lever 12, with a retaining block 14 (FIG. 7A) rigidly affixed thereto, with a screw 13 (FIG. 2) fixing lever 12 to frame 8, block 14 serving as a stop for the lever 10 when entering into notch 15 on the lever 10 (FIG. 6). The profiled lever 12 is urged from the position of FIG. 6 toward the position of FIG. 7 by a leaf spring 16 fixed at a front lower end thereof on the detachable frame 8.

The detachable frame 8 is secured with the aid of lugs 17 on the jaws 2,3 (FIG. 3) and respective U-shaped portions 18 on the detachable frame 8 (FIGS. 5 and 7), wherein the lugs 17 enter in the course of advancement of the detachable frame 8 towards the tips of the jaws 2,3 (FIG. 2). The detachable frame 8 is locked with the aid of the retaining block 14 that prevents the frame 8 from moving backwards, when the block 14 is lowered by the surgeon into a position shown in FIG. 6 to be situated in front of and engage the edge regions 30 (FIG. 3) of the jaws. The jaws 2,3 (FIG. 3) are provided with a means for releasably holding them in a position in which the guiding grooves 4 on the inner surfaces of the jaws 2,3 are approximately parallel to each other. Said means comprises a separable hinge 20 located approximately in the middle of the jaws 2,3, a spreader 21 pivoted to the rear end of the jaw 3 with a hinge 22, and carrying a swingable clamp loop 23 for surrounding the rear end of the jaw 2.

The needle-shaped anvils 6 are fixed to the jaws 2,3 with nuts 24; to allow for varying spacing there between intermediate of the curved portions of said needle-shaped anvils 6 and the front ends 25, of the jaws 2,3, several appertures 26 are provided or a set of needle-shaped anvils 6 of varying length is attached. Thus it will be seen that the portions of the jaws which are forned with the apertures 26 provide an adjusting means operatively connected with the anvils and jaws for varying the distance between the tips of the anvils and the front ends of the jaws.

The operation of the surgical instrument, in accordance with the invention, will be further described in an example of sternum stapling.

Figure 3:
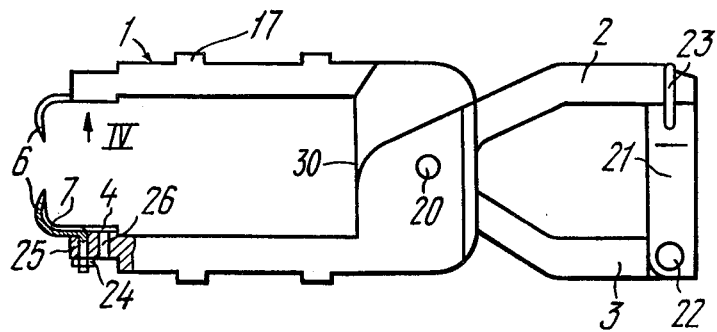
FIG. 3 is a partly sectional plan view of the anvil unit of said instrument, in accordance with the invention.
Figure 8:
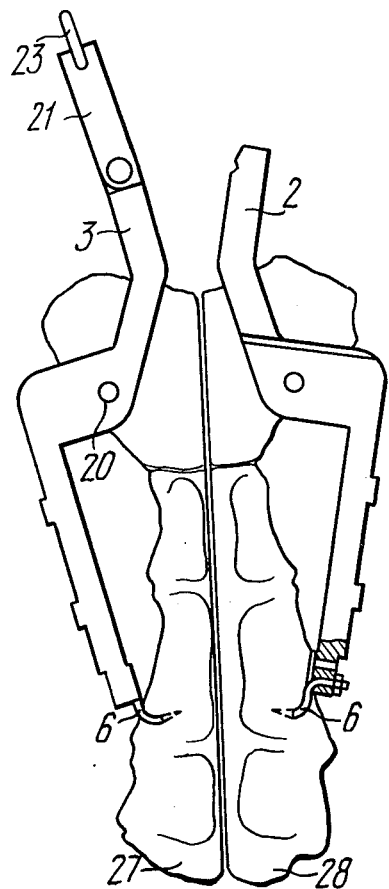
FIGS. 8, 9 and 10 depict the sequence of operation of the instrument, in accordance with the invention.
Figure 9:
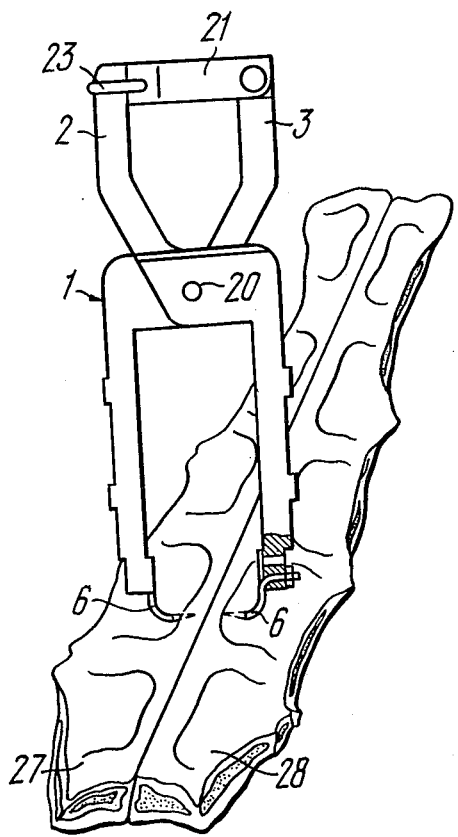
Figure 10:
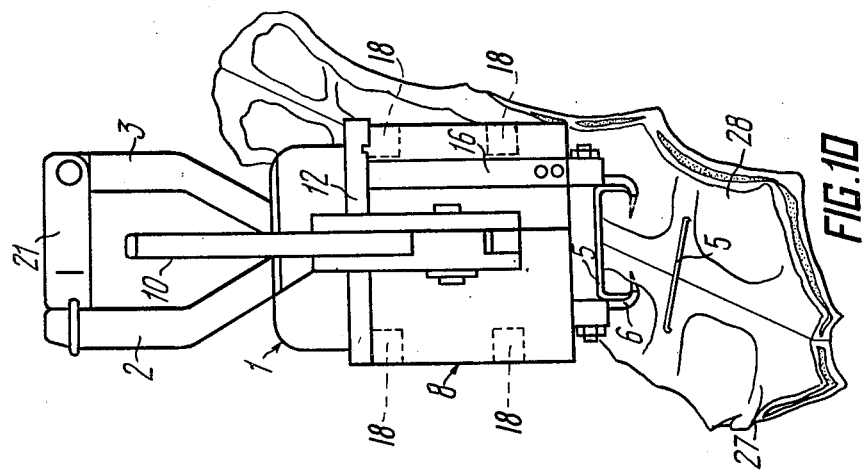

Bone tissues 27 and 28 are successively pierced with the needle-shaped anvil 6 of each jaw 2,3 (FIG. 8) on either side of the fracture line at a distance therefrom approximately equal to half the width of the staple. Thereafter, the jaws 2,3 are brought together, as shown in FIG. 9, and connected with the hinge 20, said jaws being releasably maintained parallel to each other with the spreader 21 and the loop 23. The detachable frame 8 (FIG. 10) is then applied to the thus formed anvil unit 1 of the instrument so as to interlock the U-shaped portiobns 18 (FIG. 7) with the lugs 17 of the jaws 2,3 (FIG. 10). To release lever 10 for driving member 9 (FIG. 5) pressure is applied by the surgeon in a downward direction to the profiled lever 12 which is held down, the retaining block 14 rigidly fixed to the profiled lever 12 being thereby brought down and displaced out of the notch 15 (FIG. 6), thus releasing the lever 10 and, at the same time, fixing the detachable frame 8 on the anvil unit 1 (FIG. 10) of the instrument by situating the block 14 in ront of the edge regions 30 of the jaws (FIG. 3). The instrument is ready for suturing proper.

Figure 11:
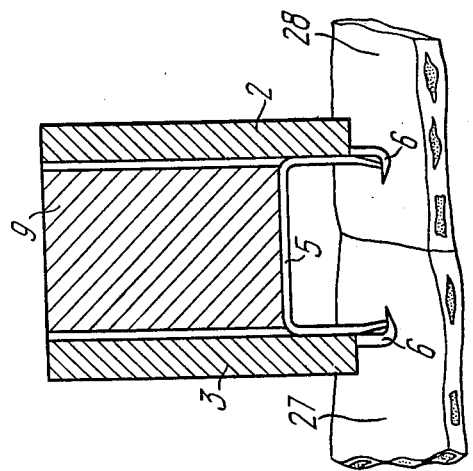
FIG. 11 is a schematic presentation of ejecting a staple in the instrument, in accordance with the invention.
Figure 12:
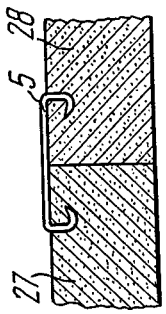
FIG. 12 shows one tissues connected with the aid of the instrument, in accordance with the invention.

Pressure on the lever 10 displaces the staple-driving member 9 forwardly (FIG. 11), and as the latter moves towards the needle-shaped anvils 6, it ejects the staple 5 from the grooves thereof. The tips of the staple 5 slide along the grooves 4 (FIG. 4) of the jaws and farther then along the grooves 7 of the needle-shaped anvils 6, bending in the latter and connecting the bone tissues 27 and 28 (FIGS. 11 and 12).

To remove the instrument, the lever 10 (FIG. 5) is returned by surgeon to its initial position. The lever 12 is released by the surgeon so that the retaining block 14 is raised by the action of spring 16 on lever 12 to enter into the notch 15, thus permitting the detachable frame 8 to be displaced from the anvil unit 1. After the frame 8 of the staple-driving unit is removed from the anvil unit 1, the jaws 2 and 3 of the latter are separaed and removed.

The next staple is applied in accordance with the above procedure.

What is claimed is:

1. A surgical instrument for suturing with metal staples, comprising an anvil unit including a pair of elongated jaws situated in alignment with each other and respectively having inner surfaces formed with guiding grooves for a staple, said jaws terminating in front ends, said unit including two anvils for bending the tips of a staple, said anvils respectively being fixed to front ends of said jaws and being shaped as needles which are curved at approximately 90° and which terminate in tips which are directed toward each other, said anvils being formed with longitudinal grooves which form extensions of said grooves of said jaws, said unit also including a means operatively connected with said jaws for releasably holding them together in a position wherein said longitudinal grooves at said inner surfaces of said jaws are approximately parallel to each other, and a staple-driving unit including a frame having means for detachably mounting the same on said jaws, said frame also being formed with grooves for receiving and holding a staple with the latter grooves also forming extensions of said jaws grooves, said staple-driving unit including a staple-driving member situated in said frame for propelling a staple toward said anvils, and said staple-driving unit also including a lever operatively connected with said staple-driving member for operating the same to propel a staple toward said anvils.

2. The combination of claim 1 and wherein said means for releasably holding said jaws together includes a hinge removably connected with said jaws for interconnecting them approximately at midportions thereof, a spreader member pivotally connected to a rear end of one of said jaws distant from the front end thereof, and a clamping loops swingably connected to said spreader member for surrounding the rear end of the other of said jaws at a location distant from said front end thereof.

3. The combination of claim 1 and wherein an adjustable means is operatively connected with said anvils and jaws for varying the distance between the tips of said anvils and the front ends of said jaws.

4. The combination of claim 2 and wherein an adjustable means is operatively connected with said anvils and said jaws for mounting said anvils adjustably on said jaws at locations which will vary the distances between the tips of said anvils and the front ends of said jaws.

5. The combination of claim 1 and wherein the grooves of said frame which receive a staple also receive said staple-driving member for guiding the latter.

6. The combination of claim 1 and wherein said frame carries a springy member which carries a blocking member, said lever being formed with a notch receiving said blocking member to hold said staple-driving member in a rear position, said blocking member being displaceable out of said notch upon depression of said springy member, for releasing said staple-driving lever to operate said staple-driving member.

7. The combination of claim 6 and wherein said blocking member when displaced from said notch becomes situated in front of edge regions of said jaws for preventing rearward movement of said frame of said staple-driving unit.

* * * * *